United States Patent
Bilenko et al.

(10) Patent No.: US 10,337,917 B2
(45) Date of Patent: Jul. 2, 2019

(54) ADJUSTABLE MULTI-WAVELENGTH LAMP

(71) Applicant: Sensor Electronic Technology, Inc., Columbia, SC (US)

(72) Inventors: Yuri Bilenko, Columbia, SC (US); Michael Shur, Latham, NY (US); Alexander Dobrinsky, Loudonville, NY (US)

(73) Assignee: Sensor Electronic Technology, Inc., Columbia, SC (US)

( * ) Notice: Subject to any disclaimer, the term of this patent is extended or adjusted under 35 U.S.C. 154(b) by 114 days.

(21) Appl. No.: 15/471,601

(22) Filed: Mar. 28, 2017

(65) Prior Publication Data

US 2017/0284866 A1   Oct. 5, 2017

Related U.S. Application Data

(60) Provisional application No. 62/316,540, filed on Mar. 31, 2016.

(51) Int. Cl.
| | |
|---|---|
| *H01J 1/62* | (2006.01) |
| *G01J 3/12* | (2006.01) |
| *G01J 3/02* | (2006.01) |
| *G01J 3/10* | (2006.01) |
| *G01N 21/25* | (2006.01) |
| *G01N 21/31* | (2006.01) |
| *G01N 21/64* | (2006.01) |
| *G01N 21/78* | (2006.01) |

(52) U.S. Cl.
CPC ............... *G01J 3/12* (2013.01); *G01J 3/027* (2013.01); *G01J 3/0267* (2013.01); *G01J 3/10* (2013.01); *G01N 21/255* (2013.01); *G01N 21/31* (2013.01); *G01N 21/645* (2013.01); *G01J 2003/1213* (2013.01); *G01N 21/78* (2013.01); *G01N 2021/3155* (2013.01); *G01N 2021/6419* (2013.01); *G01N 2201/0627* (2013.01)

(58) Field of Classification Search
None
See application file for complete search history.

(56) References Cited

U.S. PATENT DOCUMENTS

| | | | |
|---|---|---|---|
| 7,095,056 | B2 | 8/2006 | Vitta et al. |
| 7,990,045 | B2 | 8/2011 | Zukauskas et al. |
| 8,436,526 | B2 | 5/2013 | Zukauskas et al. |
| 2009/0231832 | A1 | 9/2009 | Zukauskas et al. |
| 2010/0049017 | A1 | 2/2010 | LeBoeuf et al. |
| 2011/0068698 | A1 | 3/2011 | Swoboda et al. |
| 2012/0032208 | A1 | 2/2012 | Brandes |
| 2013/0241436 | A1 | 9/2013 | Zukauskas et al. |
| 2014/0159613 | A1 | 6/2014 | Chakravarti et al. |

OTHER PUBLICATIONS

International Application No. PCT/KR2017/003543, International Search Report and Written Opinion, dated Jun. 13, 2017, 9 pages.

*Primary Examiner* — Vip Patel
(74) *Attorney, Agent, or Firm* — LaBatt, LLC

(57) ABSTRACT

An adjustable multi-wavelength lamp is described. The lamp can include a plurality of emitters. The emitters can include at least one ultraviolet emitter, at least one visible light emitter, and at least one infrared emitter. The lamp can include a control system for controlling operation of the plurality of emitters. The control system can be configured to selectively deliver power to any combination of one or more of the plurality of emitters to generate light approximating a target spectral distribution of intensity.

20 Claims, 8 Drawing Sheets

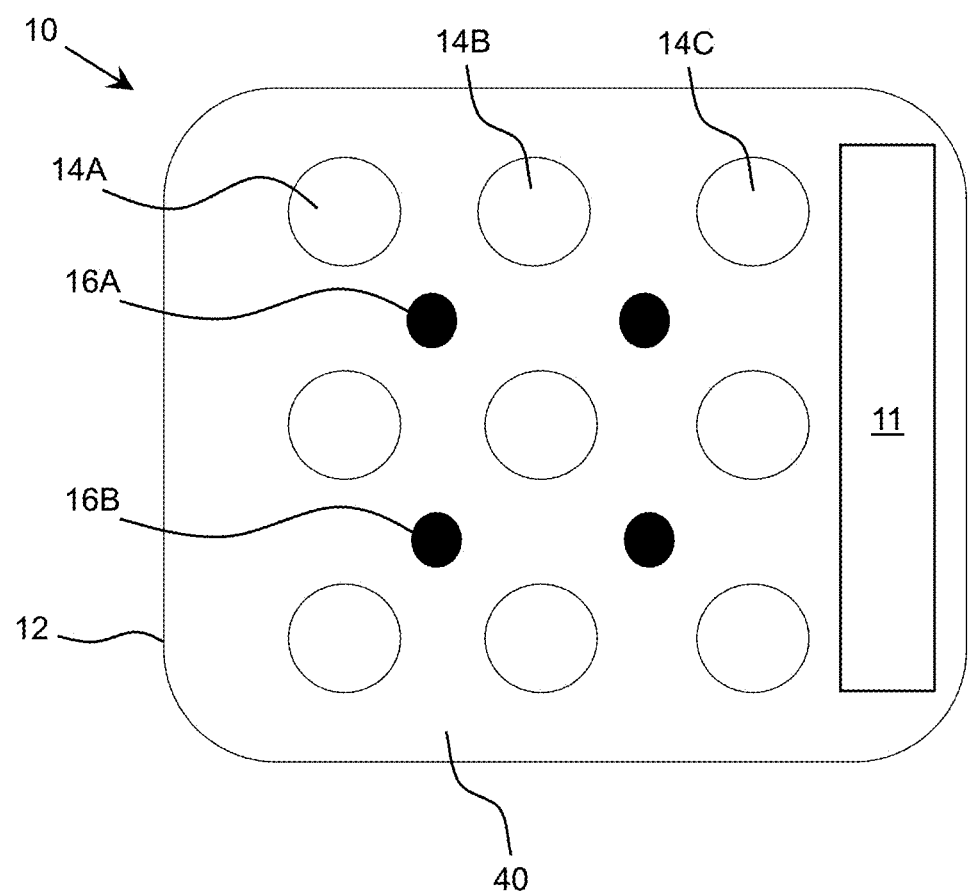

ADJUSTABLE MULTI-WAVELENGTH LAMP

REFERENCE TO RELATED APPLICATIONS

The current application claims the benefit of U.S. Provisional Application No. 62/316,540, which was filed on 31 Mar. 2016, and which is hereby incorporated by reference.

TECHNICAL FIELD

The disclosure relates generally to lighting, and more particularly, to a multi-wavelength lamp.

BACKGROUND ART

Spectroscopy refers to the use of multi-wavelength radiation to non-invasively probe a variety of samples to determine the composition, health, or function of those samples. Prior art spectroscopy is done with filtered white light sources. For example, a white light source emits a broadband radiation, which is filtered with a tunable monochromator comprising a rotating grating and slit to generate narrowband radiation, which probes a sample. Diffuse reflected radiation is then detected by an optical detector. By tuning the monochromator, it is possible to construct a spectrum of the reflected radiation, which provides non-invasive information about the sample.

Although it enables spectral measurements over a wide wavelength range, the prior art white light spectrometer suffers from a number of limitations. First, the filtered white light source has a weak signal to noise ratio. Second, the grating-based system has critical intra-system mechanical alignments, and contains moving parts, leading to a bulky and complex system with slow measurement times. Lastly, some applications employ frequency domain measurements, which are not presently possible with white light sources since white light sources cannot be easily modulated at the required 100 Mhz to 3 Ghz rates.

One prior solution to these problems is to replace the white-light source with a tunable laser. This approach eliminates the rotating grating since the laser provides a source of tunable narrow-band radiation, which requires no further filtering. However, prior art tunable semiconductor lasers are typically limited in tuning range to less than 100 nanometers (nm). For ultraviolet spectroscopy tuning, the source is particularly difficult.

SUMMARY OF THE INVENTION

Aspects of the invention provide an adjustable multi-wavelength lamp. The lamp can include a plurality of emitters. The emitters can include at least one ultraviolet emitter, at least one visible light emitter, and at least one infrared emitter. The lamp can include a control system for controlling operation of the plurality of emitters. The control system can be configured to selectively deliver power to any combination of one or more of the plurality of emitters to generate light approximating a target spectral distribution of intensity.

A first aspect of the invention provides an adjustable multi-wavelength lamp comprising: a plurality of emitters, the plurality of emitters including at least one ultraviolet emitter, at least one visible light emitter, and at least one infrared emitter; and a control system for controlling operation of the plurality of emitters, wherein the control system is configured to selectively deliver power to any combination of one or more of the plurality of emitters to generate light approximating a target spectral distribution of intensity.

A second aspect of the invention provides an analysis system comprising: an enclosure for containing a medium to be analyzed; and an adjustable multi-wavelength lamp for generating light approximating a target spectral distribution of intensity directed as the medium, the lamp including: a plurality of emitters, the plurality of emitters including at least one ultraviolet emitter, at least one visible light emitter, and at least one infrared emitter; and a control system for controlling operation of the plurality of emitters, wherein the control system is configured to selectively deliver power to any combination of one or more of the plurality of emitters to generate the light approximating the target spectral distribution of intensity.

A third aspect of the invention provides an adjustable multi-wavelength lamp comprising: a plurality of emitters, the plurality of emitters including at least one ultraviolet emitter, at least one visible light emitter, and at least one infrared emitter; a set of optical elements for adjusting a spectral distribution of intensity of light emitted by at least one of the plurality of emitters; and a control system for controlling operation of the plurality of emitters and the set of optical elements, wherein the control system is configured to selectively deliver power to any combination of one or more of the plurality of emitters to generate light approximating a target spectral distribution of intensity.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 2 shows another illustrative system including a multi-wavelength lamp according to an embodiment.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide an adjustable multi-wavelength lamp. The lamp can include a plurality of emitters. The emitters can include at least one ultraviolet emitter, at least one visible light emitter, and at least one infrared emitter. The lamp can include a control system for controlling operation of the plurality of emitters. The control system can be configured to selectively deliver power to any combination of one or more of the plurality of emitters to generate light approximating a target spectral distribution of intensity.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. As used herein, unless otherwise noted, terms of degree, such as "approximately," "substantially," and related terms, mean a reasonable amount of deviation from the stated value such that the end result is not significantly changed. For example, "approximately" can be inclusive of values within +/− ten percent of the stated value, while the term "substantially" can be inclusive of values within +/− five percent of the stated value, when such deviation would not negate the meaning of the value it modifies.

As also used herein, a medium is transparent when the medium allows at least ten percent of radiation having a target wavelength, which is radiated at a normal incidence to an interface of the medium, to pass there through. Furthermore, as used herein, a medium is reflective when the medium reflects at least ten percent of radiation having a target wavelength, which is radiated at a normal incidence to an interface of the medium.

Figure 1:
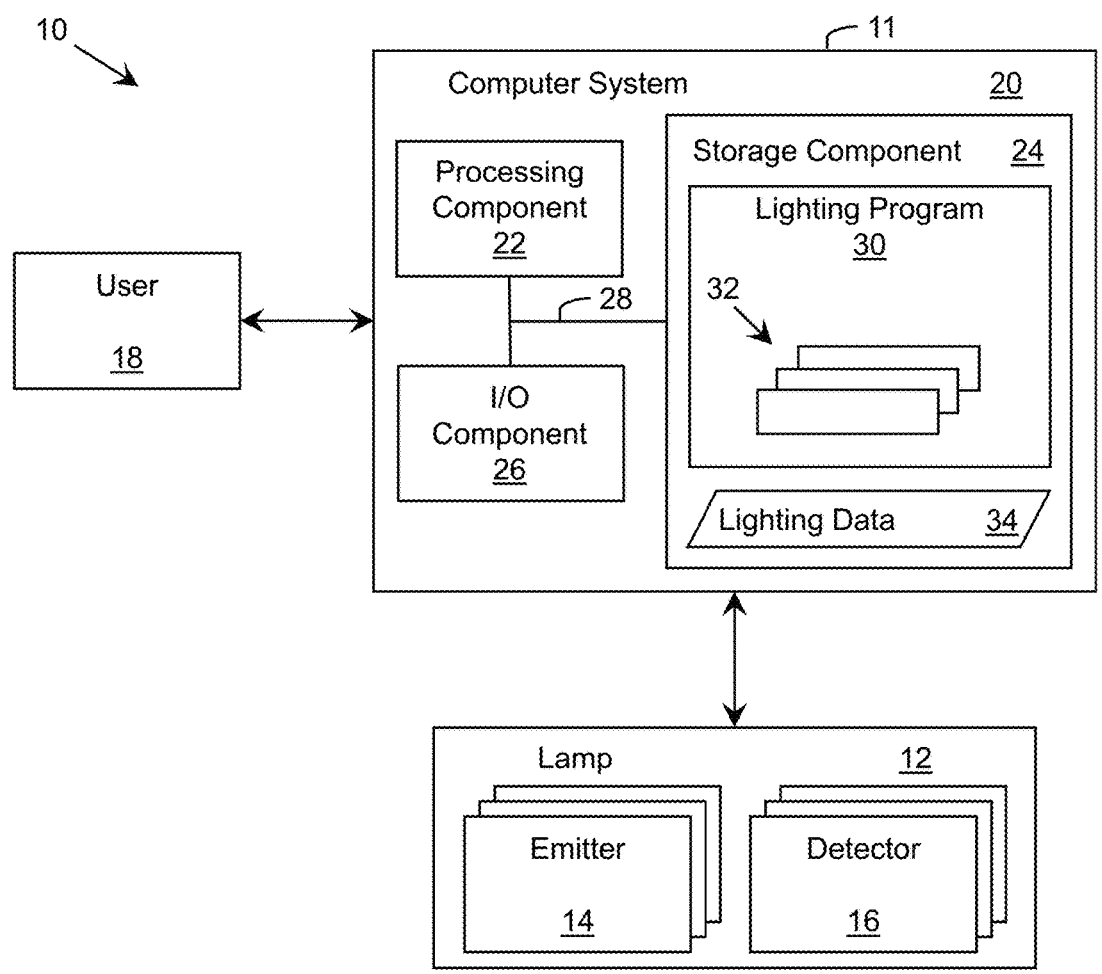
FIG. 1 shows an illustrative multi-wavelength lighting system according to an embodiment.

Turning to the drawings, FIG. 1 shows an illustrative multi-wavelength lighting system 10 according to an embodiment. To this extent, the system 10 includes a control system 11, shown implemented as a computer system 20, that can perform a process described herein in order to operate a lamp 12 to generate adjustable multi-wavelength light. In particular, the computer system 20 is shown including a lighting program 30, which makes the computer system 20 operable to generate adjustable multi-wavelength light using the lamp 12 by performing a process described herein. In an embodiment, the computer system 20 can further receive and process data regarding detected multi-wavelength light emitted by and/or received at the multi-wavelength lamp 12.

The computer system 20 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, the processing component 22 executes program code, such as the lighting program 30, which is at least partially fixed in storage component 24. While executing program code, the processing component 22 can process data, which can result in reading and/or writing transformed data, such as lighting data 34, from/to the storage component 24 and/or the I/O component 26 for further processing. The pathway 28 provides a communications link between each of the components in the computer system 20.

The I/O component 26 can comprise one or more human I/O devices, which enable a human user 18 to interact with the computer system 20 and/or one or more communications devices to enable a system user 18 to communicate with the computer system 20 using any type of communications link. To this extent, the lighting program 30 can manage a set of interfaces (e.g., graphical user interface(s), application program interface, and/or the like) that enable human and/or system users 18 to interact with the lighting program 30 and the lighting data 34. Furthermore, the lighting program 30 can manage (e.g., store, retrieve, create, manipulate, organize, present, etc.) the data, such as lighting data 34, using any solution.

The I/O component 24 also can comprise one or more I/O interfaces and/or devices, which enables the computer system 20 to operate and/or receive data from the lamp 12. In an embodiment, the I/O component 24 and lamp 12 are configured to enable the computer system 20 to selectively operate each of a plurality of emitters 14 individually. Alternatively, the I/O component 24 and lamp 12 can be configured to enable the computer system 20 to selectively operate sub-groups of the plurality of emitters 14 individually. In the latter case, a sub-group can be defined as a group of emitters 14 configured to generate light having substantially the same peak wavelength. Similarly, the I/O component and lamp 12 can be configured to enable the computer system 20 to selectively operate a plurality of detectors 16 individually or a sub-groups as described herein.

In any event, the computer system 20 can comprise one or more general purpose computing articles of manufacture (e.g., computing devices) capable of executing program code, such as the lighting program 30, installed thereon. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, the lighting program 30 can be embodied as any combination of system software and/or application software.

Furthermore, the lighting program 30 can be implemented using a set of modules 32. In this case, a module 32 can enable the computer system 20 to perform a set of tasks used by the lighting program 30, and can be separately developed and/or implemented apart from other portions of the lighting program 30. As used herein, the term "component" means any configuration of hardware, with or without software, which implements the functionality described in conjunction therewith using any solution, while the term "module" means program code that enables a computer system 20 to implement the actions described in conjunction therewith using any solution. When fixed in a storage component 24 of a computer system 20 that includes a processing component 22, a module is a substantial portion of a component that implements the actions. Regardless, it is understood that two or more components, modules, and/or systems may share some/all of their respective hardware and/or software. Furthermore, it is understood that some of the functionality discussed herein may not be implemented or additional functionality may be included as part of the computer system 20.

When the computer system 20 comprises multiple computing devices, each computing device can have only a portion of the lighting program 30 fixed thereon (e.g., one or more modules 32). However, it is understood that the computer system 20 and the lighting program 30 are only representative of various possible equivalent computer systems that may perform a process described herein. To this extent, in other embodiments, the functionality provided by the computer system 20 and the lighting program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 20 includes multiple computing devices, the computing devices can communicate over any type of communications link. Furthermore, while performing a process described herein, the computer system 20 can communicate with one or more other computer systems using any type of communications link. In either case, the communications link can comprise any combination of various types of optical fiber, wired, and/or wireless links; comprise any combination of one or more types of networks; and/or utilize any combination of various types of transmission techniques and protocols.

As discussed herein, the control system 11 is configured to operate components of the lamp 12 to generate and/or detect multi-wavelength light. In an illustrative embodiment, the lamp 12 includes emitters 14 configured to generate light having peak emissions within the ultraviolet, visible, and infrared spectrums. In a more particular embodiment, the emitters 14 include light emitting diodes (LEDs) or laser diodes, with at least one emitter 14 configured to generate light having a peak emission wavelength for each of the ultraviolet, visible, and infrared spectrums. To this extent, the emitters 14 can include: one or more ultraviolet LEDs; one or more visible LEDs; and one or more infrared LEDs. In a still more particular embodiment, the emitters can comprise solid-state LEDs. An ultraviolet emitter can comprise a group III nitride semiconductor device, such as an ultraviolet LED fabricated from semiconductor layers epitaxially grown on a substrate, such as a sapphire substrate or other suitable substrate.

It is understood that the emitters 14 and/or groups of emitters (e.g., the UV, visible, and infrared emitters) can include emitters configured to emit light having different peak emissions (e.g., within the UV, visible, or infrared spectrum) as well as different spectral distributions of intensity (e.g., as defined by the full width at half maximum (FWHM) for the emitted light). In an embodiment, the FWHM for an emitter is at least 10 nm. As discussed herein, each emitter 14 can be independently operated by the control system 11, e.g., by an independent voltage bias. Additionally, each emitter 14 or a group of emitters 14 can have a particular set of optical elements providing the emitter 14 or group of emitters 14 with unique lighting characteristics. For example, the emitters 14 may include multiple emitters 14 having the same peak wavelength but different spectral distributions of intensity. In this case, one emitter can emit light having a focused intensity distribution, while another emitter can emit light having a diffusive intensity distribution.

FIG. 2 shows another illustrative system 10 including a multi-wavelength lamp 12 according to an embodiment. In this case, the lamp 12 and the control system 11 are implemented in a single housing, which includes any necessary electronic components, wiring, and/or the like, which are not shown for clarity, to enable operation of the lamp 12 and the control system 11 as described herein. To this extent, the control system 11 can comprise a control module for controlling operation of the lamp 12. In an embodiment, the control system 11 can individually operate each of the emitters 14A-14C and detectors 16A, 16B. The control system 11 can individually operate the emitters 14A-14C in a continuous or pulsed mode. The control system 11 can generate pulses of different duration, frequency, and/or the like, for different emitters 14A-14C.

The lamp 12 is shown including nine emitters 14A-14C and four detectors 16A-16B. However, it is understood that the number of and arrangement of emitters 14A-14C and detectors 16A-16B included in the lamp 12 is only illustrative of various possible embodiments of a lamp described herein. Regardless, as described herein, the lamp 12 can include emitters 14A-14C that emit light having distinct properties. For example, as a non-limiting example, the emitter 14A can emit ultraviolet light, the emitter 14B can emit visible light, and the emitter 14C can emit infrared light. The remaining emitters (not labeled) can emit substantially the same light as one of the emitters 14A-14C or light with a different peak wavelength and/or intensity distribution as described herein.

Similarly, the detectors 16A, 16B can be sensitive to a broad spectrum of light or light of a narrower band of wavelengths. Illustrative detectors 16A, 16B include optical sensors, photodetectors, fluorescent sensors, infrared sensors, etc. In an illustrative embodiment, the control system 11 can be configured to operate a device in forward bias as an emitter and in reverse bias as a photodetector. In this case, the control system 11 can selectively operate one or more of the emitters 14A-14C and detectors 16A, 16B shown in the lamp 12 as either an emitter or a photodetector. The control system 11 can dynamically vary the emitters emitting light and the emitters operated as photodetectors during operation of the lamp 12. Furthermore, the control system 11 can evaluate the distribution of intensity of a first subset of emitters using data acquired by a second subset of emitters operated as photodetectors.

The control system 11 can use data acquired by the detectors 16A, 16B to evaluate the intensity of radiation delivered over an area. For example, the lamp 12 can acquire data regarding a spatial distribution of intensity of the light emitted by the emitters 14A-14C using an array of photodetectors 16A, 16B. The control system 11 can record, store, and compare spatial distribution of intensity patterns as lighting data 34. Similarly, the control system 11 can process data acquired by the photodetectors 16A, 16B to evaluate one or more attributes of a medium. Illustrative attributes include fluorescence, reflectance, transmission, radiated heat, and/or the like. Furthermore, the control system 11 can dynamically evaluate a spatial distribution of intensity and adjust the bias(es) applied to one or more emitters 14A-14C based on the feedback to achieve a target spatial distribution of intensity. For example, the control system 11 can adjust a duration of pulses of different emitters 14A-14C to affect changes to the spatial and temporal distribution of intensity.

In an embodiment, a surface 40 of the lamp 12 can include one or more features to assist in the emission and/or detection of light. For example, the surface 40 can be reflective of light emitted by the emitters 14A-14C. Such a reflective surface can be formed of any reflective material, such as polished aluminum, a fluoropolymer such as polytetrafluoroethylene (PTFE), a reflective polymer (e.g., Teflon), and/or the like. Additionally, the surface 40 can be shaped (e.g., curved), the lamp 12 can include one or more additional optical elements, such as transparent lens(es), and/or the like, to form a beam from the emitted light.

Figure 3A:
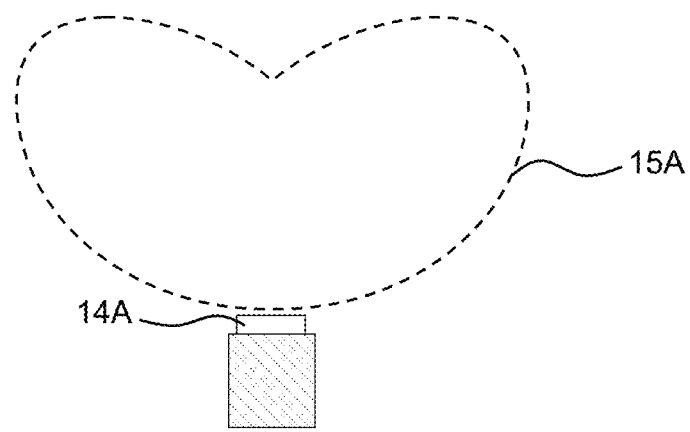
FIGS. 3A and 3B show illustrative emitters having different spatial emission patterns according to an embodiment.
Figure 3B:
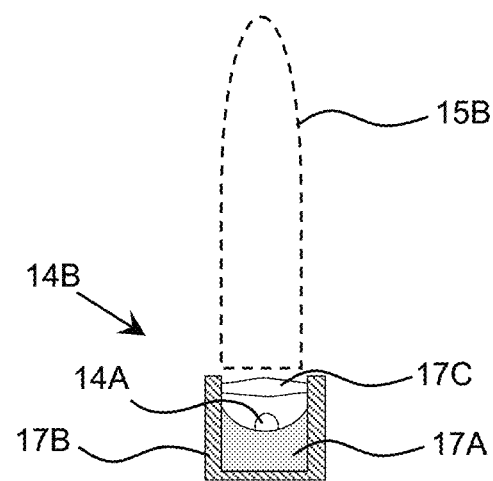

In an embodiment, the emitters 14A-14C can be configured to emit light having differing spatial distributions. To this extent, FIGS. 3A and 3B show illustrative emitters 14A, 14B having different spatial emission patterns 15A, 15B, respectively, according to an embodiment. As illustrated in FIG. 3A, the emitter 14A can comprise a light source, such as a light emitting diode, that emits light having a distributed (diffusive) emission pattern 15A. In FIG. 3B, the emitter 14B is configured to emit light having a focused emission pattern 15B.

A focused (or distributed) emission pattern can be generated by the light emitting device. Alternatively, as illustrated in FIG. 3B, the emitter 14B can include one or more optical elements to generate a desired emission pattern. For example, the emitter 14B can include a light emitting device 14A, which emits light having a distributed emission pattern 15A as shown in FIG. 3A. The light emitting device 14A can be mounted on a submount 17A having a reflective, concaved surface, which can focus the light emission pattern 15B. Additionally, the emitter 14B can include a housing 17B in which the light emitting device 14A is mounted, which includes reflective sides extending above the light emitting device 14A to focus the light emission pattern 15B. Still further, the emitter 14B can include a transparent lens 17C, which can adjust the direction of rays to create the focused light emission pattern 15B.

While various features have been shown in conjunction with generating a focused emission pattern 15B, it is understood that embodiments of an emitter can include similar optical elements to generate any type of emission pattern, including a distributed emission pattern. Additionally, it is understood that embodiments of an emitter can include any combination of one or more of the optical elements 17A-17C and/or alternative optical elements. Still further, an embodiment of an emitter can have a variable emission pattern. For example, an emitter can include one or more optical elements oriented with respect thereto, and the control system 11 can selectively adjust the relative arrangement of the optical element(s) and the emitter to adjust the emission pattern (e.g., adjust the FWHM of the emission pattern).

Figure 4A:
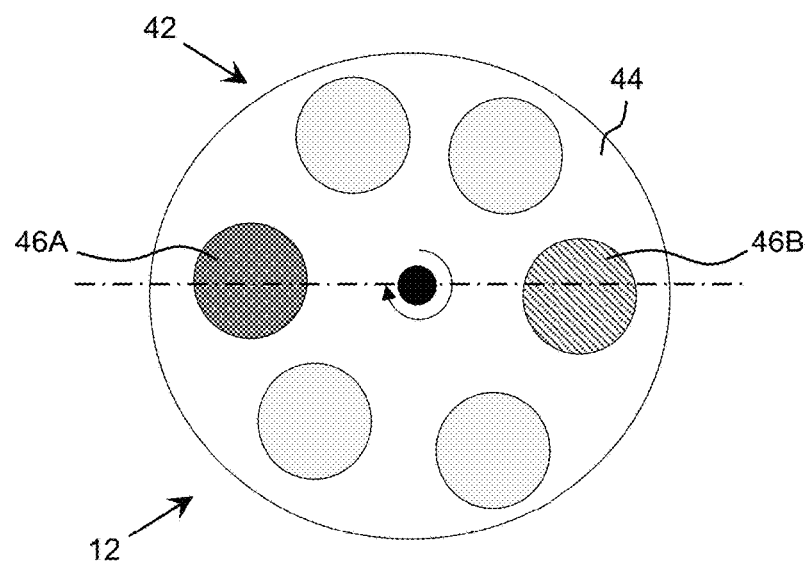
FIGS. 4A and 4B show a top and side cross section view, respectively, of an illustrative lamp including a filtering mechanism according to an embodiment.
Figure 4B:
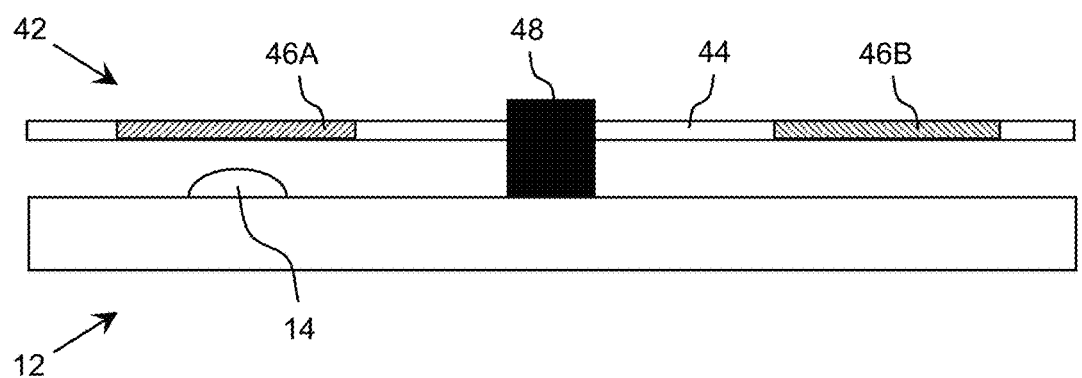

An embodiment of the lamp 12 can combine the use of emitters emitting light of different wavelengths with one or more filters. For example, FIGS. 4A and 4B show a top and side cross section view, respectively, of an illustrative lamp including a filtering mechanism 42 according to an embodiment. As illustrated, the filtering mechanism 42 can include rotatable member 44 including a plurality of filters 46A, 46B, each of which can be configured to filter different wavelengths of light. The rotatable member 44 can be mounted to a rotatable shaft 48, which can be operated by the control system 11 (FIG. 1) in order to selectively place a filter 46A, 46B above an emitter 14, resulting in a desired removal of an intensity of light emitted by the emitter 14 at a desired set of wavelengths.

It is understood that the filtering mechanism 42 is only illustrative of various filtering mechanisms that can be utilized. To this extent, the number, orientation, and shape of the filters 46A, 46B are only illustrative and embodiments of the invention are not limited thereto. Similarly, the manner in which different filters 46A, 46B are selectively moved is only illustrative of numerous solutions that can be implemented in embodiments. Additionally, it is understood that the rotatable member 44 can include one or more regions in which no light is filtered, and all of the light emitted by the emitter 14 is allowed to pass there through.

The filters 46A, 46B can be formed of any combination of various types of filters. For example, a filter can comprise a band pass filter. Alternatively, a filter can comprise a Bragg mirror. The filters can also include polarization filters, filters that absorb a set of wavelengths and transmit a set of wavelength and/or the like.

A lamp described herein can be manufactured and/or operated to approximate a target absorption, fluorescence, reflection spectrum, and/or the like, of a target medium. In an embodiment, the lamp is utilized as part of a process for substantially matching the absorption, fluorescence, reflection spectrum, and/or the like, of the target medium by separately delivering power to one or more of the emitters of the lamp. Operation of the lamp also can include operating (e.g., moving, adjusting, and/or the like), one or more optical elements to adjust the spatial distribution, spectral distribution, intensity, and/or the like, of the emitted radiation. The process can result in a targeted distribution of spectral peaks and/or spatial distribution of intensity over an area of an object, target medium, and/or the like.

Figure 5:
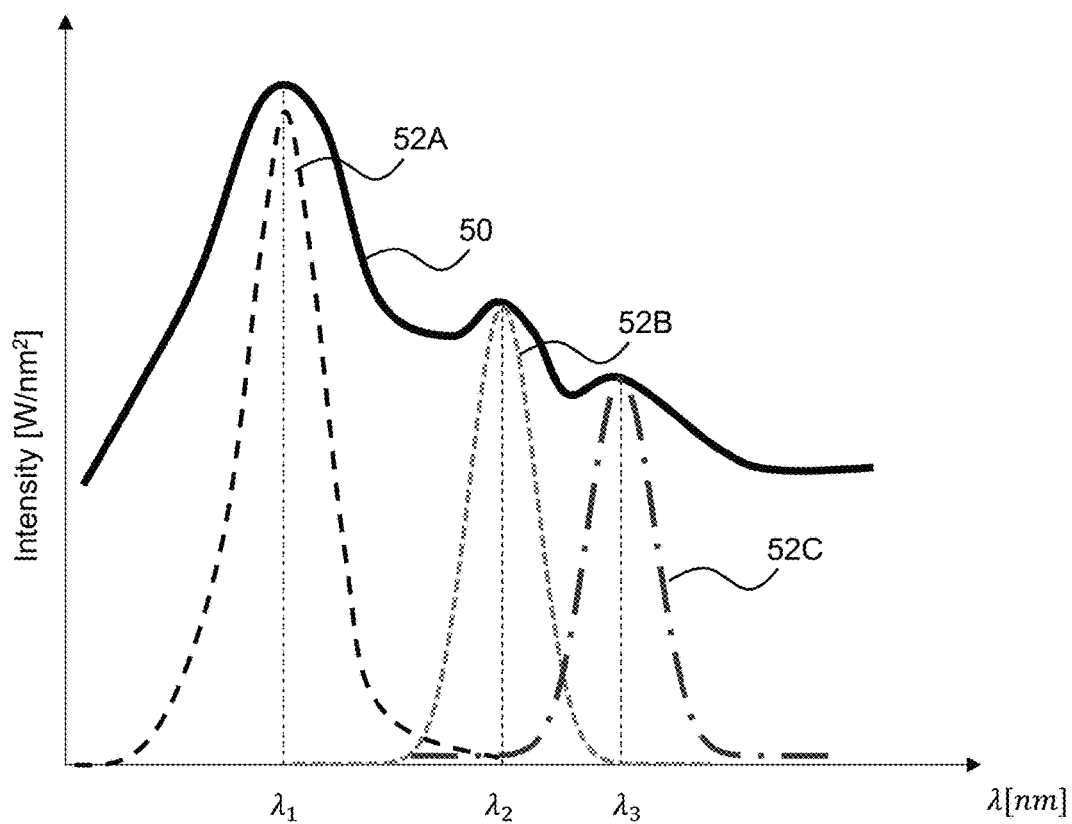
FIG. 5 shows an illustrative curve illustrating approximation of a spectrum using a multi-wavelength lamp described herein according to an embodiment.

For example, FIG. 5 shows an illustrative curve illustrating approximation of a spectrum 50 using a multi-wavelength lamp described herein according to an embodiment. As illustrated, a target spectrum 50, which can correspond to absorption of a particular material for example, can be approximated using a lamp described herein by operating multiple emitters to emit light having emission patterns 52A-52C with differing peak wavelengths $\lambda_1$-$\lambda_3$ and differing intensities to create an appropriate distribution of spectra peaks. As illustrated, each emission pattern 52A-52C can have a peak wavelength $\lambda_1$-$\lambda_3$ that corresponds to a local peak of the target spectrum 50. Additionally, one or more optical elements (e.g., filters) can be used to remove undesirable peaks. While the use of three emitters having relatively narrow emission spectra are illustrated, it is understood that any number of emitters having any combination of various emission patterns can be utilized to approximate a target spectrum 50. The selection of a number of emitters utilized can be based on a required accuracy with which the target spectrum 50 is to be approximated.

In an embodiment, a lamp described herein can be utilized in a spectroscopic experiment. Through the selective operation of the various emitters, and possibly detectors, the lamp can be designed and tailored for any one of multiple distinct spectroscopic experiments. To this extent, the lamp emitters and detectors can be operated to illuminate a medium with light and detect absorption, reflection, and/or transmission of the light by, from, and/or through the medium. The control system 11 can acquire and analyze data corresponding to noise spectra of the light emitters and/or photodetectors. The computer system can further acquire and analyze data corresponding to a distribution of the noise responses across an area of a surface being irradiated. Furthermore, the detectors can be operated to detect fluorescence of the medium. For example, the detectors can include fluorescent sensors designed to acquire data corresponding to the emittance in a target wavelength of the medium being radiated.

In an illustrative embodiment, the medium is a fluid, such as a liquid or gas. In a more particular illustrative embodiment, the lamp can be utilized to evaluate absorption of the fluid in any of various ranges of ultraviolet light. Illustrative ranges of ultraviolet light include 230-300 nm, 280-300 nm, and 230-1500 nm. In an embodiment, the range of ultraviolet light includes 230-360 nm, which corresponds, for example, to the absorbance of biological fluids such as uric acid.

Figure 6:
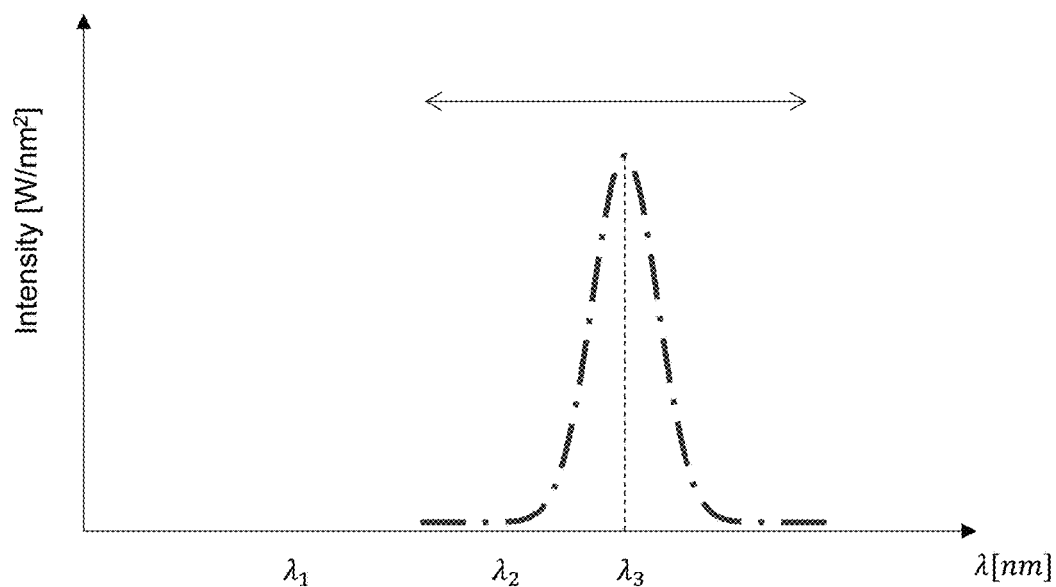
FIG. 6 shows how the peak wavelength emitted from a lamp described herein can be shifted according to an embodiment.

As part of the spectroscopic experiment, the control system 11 can operate the lamp 12 to shift a peak wavelength of the light emitted therefrom in order to probe a sample. FIG. 6 shows how the peak wavelength of light emitted from a lamp described herein can be shifted according to an embodiment. In this case, the control system 11 can selectively turn on or off emitters of the lamp that emit light having differing peak wavelengths $\lambda_1$-$\lambda_3$. For example, to adjust the peak wavelength to a smaller wavelength, the control system 11 can turn off an emitter emitting light having a peak wavelength $\lambda_3$ and turn on an emitter emitting light having a peak wavelength $\lambda_2$.

While three peak wavelengths $\lambda_1$-$\lambda_3$ are shown in FIG. 6, it is understood that a lamp described herein can include any number of emitters configured to emit light at differing peak wavelengths. Such emitters can be selected to cover a broad spectrum of radiation. For example, the spectrum can range from infrared radiation to ultraviolet radiation. Adjacent peak wavelengths along the spectrum for emitters included in a lamp can be separated by any suitable amount of wavelengths for the application. For a substantially continuous shift of the peak wavelength emitted by the lamp, the adjacent peak wavelengths can be relatively close.

In addition to selectively turning on and off emitters of light with differing peak wavelengths, an embodiment of the lamp can utilize optical elements to create a desired peak wavelength. For example, the computer system can operate two adjacent emitters to emit light of differing peak wavelengths and adjust the relative biases applied to each emitter and/or use filter(s) to cause the lamp to emit light having a peak wavelength located between the two peak wavelengths.

In an embodiment, the lamp can be configured and operated to detect and/or eliminate a particular set of chemicals. In a more particular illustrative embodiment, the lamp can be configured and operated to detect and/or eliminate uric acid. For example, the UV absorption of a liquid that may contain uric acid can be monitored and compared to an absorption chart to infer a concentration of uric acid in the liquid. In a more particular embodiment, the liquid is spent dialysate. Other chemicals that can be monitored through UV absorption spectroscopy in spent dialysate can include, creatinine, potassium, and phosphate.

In addition to varying spectral distributions, an embodiment of the lamp can be operated to generate light having a varying spatial distribution. The spatial distribution of the light can be non-uniform, including one or more intensity peaks and/or intensity valleys across a two-dimensional physical space being illuminated by the lamp. The variation in intensity can exceed that of any unintentional variations due to the limits of manufacturing. The locations of the physical space having the higher or lower intensities can be selected using any criteria suitable for the application. Similarly, the extent of the higher or lower intensities can be selected according to the particular application.

Figure 7:
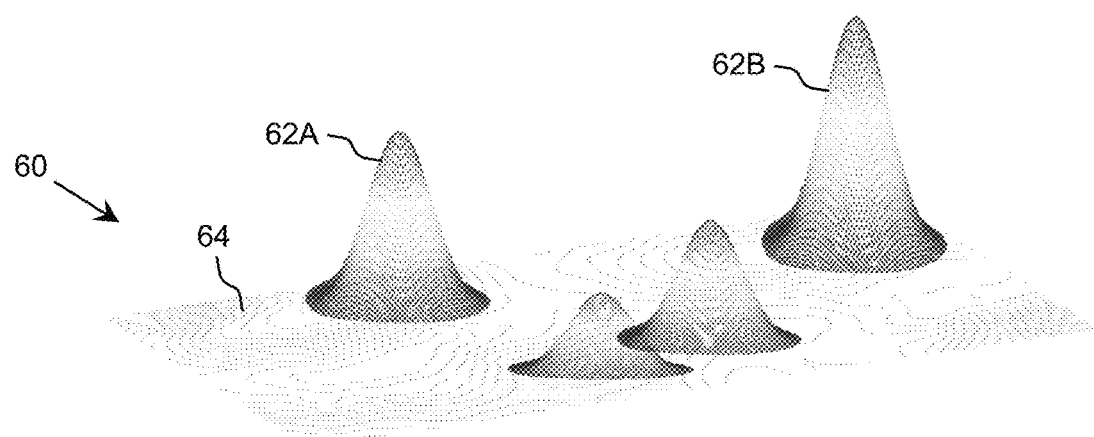
FIG. 7 shows an illustrative non-uniform spatial distribution of intensity of light emitted by an embodiment of a lamp described herein.

FIG. 7 shows an illustrative non-uniform spatial distribution of intensity 60 of light emitted by an embodiment of a lamp described herein. As illustrated, the spatial distribution of intensity 60 over a two dimensional surface can include multiple peaks 62A, 62B, each of which corresponds to a high intensity of light at the corresponding location on the surface. Two or more peaks 62A, 62B can correspond to light having the same peak wavelength or light having different peak wavelengths. For example, the peak 62A can correspond to a high intensity of ultraviolet light, while the peak 62B can correspond to a high intensity of visible light. The flat areas 64 can correspond to regions of low intensity of light across the entire spectrum.

The spatial distribution of the UV intensity can be selected depending on a set of articles being irradiated. For example, the peaks 62A, 62B of high intensity light can be focused on the article(s) being presented. In an embodiment, the lamp can further comprise emitters designed to induce a fluorescent signal from the article(s) being irradiated. The fluorescent signal can be used to evaluate the presence of contamination of the article surface by bacteria, viruses, and/or other materials emitting distinct fluorescent signatures. In an embodiment, a spatial distribution of the intensity of the light can be selected based on the sensed fluorescent signal(s) from different areas of the irradiated surface.

Figure 8:
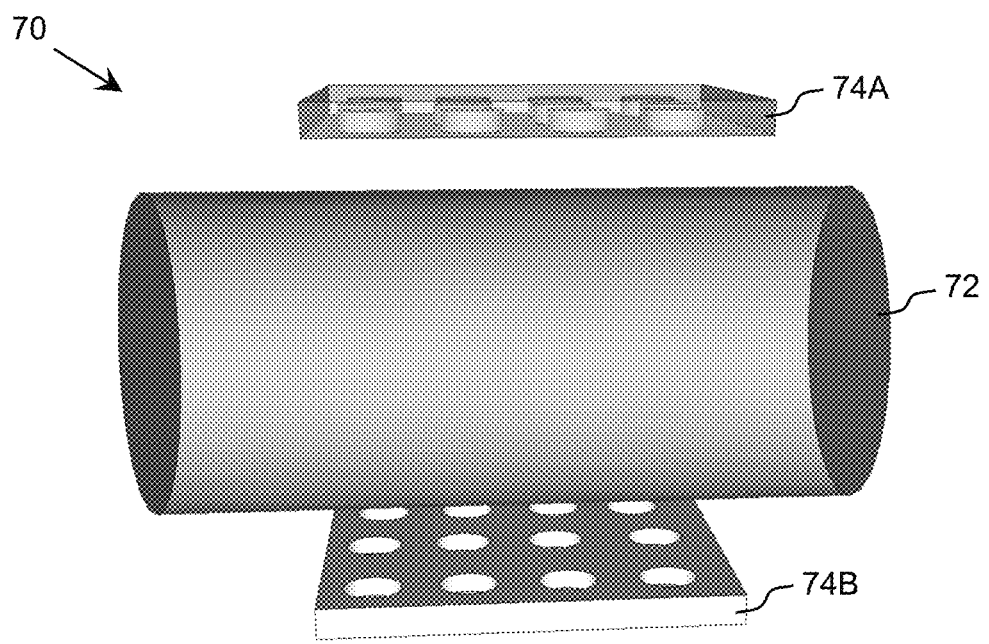
FIG. 8 shows an illustrative analysis system according to an embodiment.

A multi-wavelength lamp described herein can be implemented as part of a system including other components. For example, FIG. 8 shows an illustrative analysis system 70 according to an embodiment. The analysis system 70 includes an enclosure 72 for containing a medium for which the corresponding absorbance, reflectance, transmittance, and/or the like, is to be analyzed. Such a medium can comprise a liquid, such as spent dialysate or any other relevant biological liquid, which has a distinct UV absorption based on the chemical composition of the liquid. In another embodiment, the medium can comprise a flowable polymer, such as printable ink. The enclosure 72 walls are transparent to light of wavelengths used to analyze the medium. The analysis system 70 includes a pair of analysis components 74A, 74B located on opposing sides of the enclosure 72. In an embodiment, the analysis component 74A includes a set of multi-wavelength lamps and the analysis component 74B includes a set of photodetectors.

During operation of the system 70, the set of multi-wavelength lamps can be operated to generate light as described herein, while the set of photodetectors can be operated to acquire data regarding one or more attributes of the medium being analyzed. In another embodiment of the system 70, each of the analysis components 74A, 74B can include a set of multi-wavelength lamps. In this case, each multi-wavelength lamp can include a set of photodetectors or one or more emitters can be operated in reverse bias as a photodetector during the analysis process. To this extent, during an analysis, the components 74A, 74B can each be operated to emit light and operated to detect light.

Figure 9:
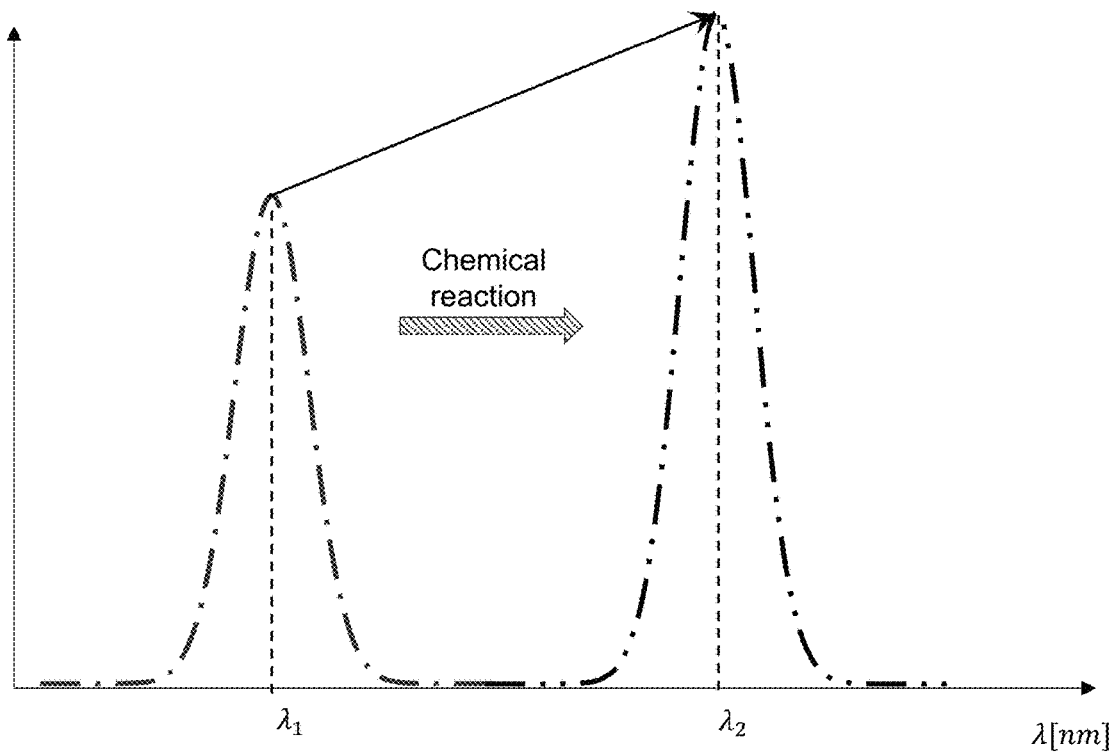
FIG. 9 shows an illustrative change in absorption peak wavelength and intensity due to a chemical reaction according to an embodiment.

In an embodiment, a multi-wavelength lamp described herein can be utilized as part of a process to determine a chemical substance. For example, using the system 70 or a similar system, the multi-wavelength lamp(s) can be utilized to detect changes in an absorption peak of the medium in the enclosure 72 due to, for example, occurrence of a chemical reaction. In this case, the medium (e.g., one or more chemical substances) can be evaluated during a first emission test using the analysis components 74A, 74B. Subsequently, the medium can undergo a chemical reaction, which results in a changed absorbance characteristics of the resulting medium. For example, FIG. 9 shows an illustrative change in absorption peak wavelength and intensity due to a chemical reaction according to an embodiment. The medium can be evaluated during a second emission test using the analysis components 74A, 74B to evaluate an occurrence of the chemical reaction, progress of the chemical reaction, a type of chemical substance in the enclosure 72, and/or the like. In particular, the medium can be evaluated to determine whether the absorption peak wavelength has changed in a manner predicted after the chemical reaction. This process can be continued for a series of chemical reactions. The measurements of absorbance spectra can be used to find a concentration of several chemical substances within the medium.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. An adjustable multi-wavelength lamp comprising:
a plurality of emitters, the plurality of emitters including at least one ultraviolet emitter, at least one visible light emitter, and at least one infrared emitter; and
a control system for controlling operation of the plurality of emitters, wherein the control system is configured to selectively deliver power to any combination of one or more of the plurality of emitters to generate light approximating a target spectral distribution of intensity.

2. The lamp of claim 1, wherein the target spectral distribution of intensity corresponds to one of: an absorption, a fluorescence, or a reflection spectrum, of a medium.

3. The lamp of claim 1, further comprising a set of optical elements for adjusting at least one of: a spectral distribution of intensity or a spatial distribution, of light emitted by at least one of the plurality of emitters.

4. The lamp of claim 3, wherein the control system is further configured to operate at least one of the set of optical elements to selectively adjust the at least one of: the spectral distribution of intensity or the spatial distribution.

5. The lamp of claim 3, wherein the set of optical elements includes at least one optical element for focusing light emitted by the at least one of the plurality of emitters.

6. The lamp of claim 1, wherein the control system is configured to selectively operate at least one of the plurality of emitters as a photodetector.

7. The lamp of claim 1, further comprising a set of detectors, wherein the control system is configured to evaluate a medium using data acquired by the set of detectors.

8. The lamp of claim 1, wherein the control system adjusts the power delivered based on the target spectral distribution of intensity and data acquired from a set of detectors corresponding to an actual spectral distribution of intensity of light emitted by the lamp.

9. An analysis system comprising:
an enclosure for containing a medium to be analyzed; and
an adjustable multi-wavelength lamp for generating light approximating a target spectral distribution of intensity directed as the medium, the lamp including:
a plurality of emitters, the plurality of emitters including at least one ultraviolet emitter, at least one visible light emitter, and at least one infrared emitter; and
a control system for controlling operation of the plurality of emitters, wherein the control system is configured to selectively deliver power to any combination of one or more of the plurality of emitters to generate the light approximating the target spectral distribution of intensity.

10. The system of claim 9, wherein the target spectral distribution of intensity corresponds to one of: an absorption, a fluorescence, or a reflection spectrum, of the medium.

11. The system of claim 9, wherein the lamp further includes a set of optical elements for adjusting at least one of: a spectral distribution of intensity or a spatial distribution, of light emitted by at least one of the plurality of emitters.

12. The system of claim 9, wherein the control system is configured to selectively operate at least one of the plurality of emitters as a photodetector.

13. The system of claim 9, further comprising a set of detectors, wherein the system includes means for devaluating the medium using data acquired by the set of detectors.

14. The system of claim 13, wherein the set of detectors are located on an opposing side of the enclosure as the lamp.

15. The system of claim 14, wherein the set of detectors are located on a second adjustable multi-wavelength lamp, and wherein the set of detectors include at least one of a plurality of emitters operating as a photodetector.

16. The system of claim 9, wherein the medium is a fluid and the analysis includes determining an occurrence of a chemical reaction.

17. An adjustable multi-wavelength lamp comprising:
a plurality of emitters, the plurality of emitters including at least one ultraviolet emitter, at least one visible light emitter, and at least one infrared emitter;
a set of optical elements for adjusting a spectral distribution of intensity of light emitted by at least one of the plurality of emitters; and
a control system for controlling operation of the plurality of emitters and the set of optical elements, wherein the control system is configured to selectively deliver power to any combination of one or more of the plurality of emitters to generate light approximating a target spectral distribution of intensity.

18. The lamp of claim 17, wherein the control system is configured to selectively operate at least one of the plurality of emitters as a photodetector.

19. The lamp of claim 18, wherein the control system dynamically adjusts operation of at least one of the plurality of emitters or at least one of the set of optical elements based on data acquired by the photodetector.

20. The lamp of claim 17, wherein the control system evaluates a medium for a presence of a chemical using data acquired by the photodetector.

* * * * *